United States Patent [19]

Hasegawa et al.

[11] Patent Number: 4,663,315
[45] Date of Patent: May 5, 1987

[54] DEVICE AND METHOD FOR VAPORIZING THERMALLY VAPORIZABLE COMPOSITION

[75] Inventors: Takahiro Hasegawa; Takanobu Kashihara; Akira Nishimura, all of Ako, Japan

[73] Assignee: Earth Chemical Company, Limited, Hyogo, Japan

[21] Appl. No.: 797,196

[22] Filed: Nov. 14, 1985

Related U.S. Application Data

[62] Division of Ser. No. 639,299, Aug. 10, 1984, abandoned.

[30] Foreign Application Priority Data

Jan. 31, 1984 [JP] Japan ................................ 59-16760
May 7, 1984 [JP] Japan ................................ 59-91554

[51] Int. Cl.⁴ .................... A01N 57/10; A61L 9/02; A61L 9/03; C09K 3/30
[52] U.S. Cl. ................................ 514/86; 239/44; 239/47; 252/1; 252/305; 252/522 R; 424/76; 514/530; 514/531; 514/918; 514/957

[58] Field of Search ............ 252/1, 305, 522 R; 424/43, 76; 514/530, 531, 918, 957, 86; 239/44, 47

[56] References Cited

U.S. PATENT DOCUMENTS

| 3,039,921 | 6/1962 | Brandenburg et al. ......... 252/305 X |
| 3,482,929 | 12/1969 | Gentil .............................. 239/44 X |
| 3,633,881 | 1/1972 | Yurdin ............................. 239/44 X |
| 3,791,983 | 2/1974 | Maierson ............................ 252/305 |
| 3,943,239 | 3/1976 | Yamaguchi et al. ................ 424/43 |
| 4,069,308 | 1/1978 | Tanaka .............................. 424/43 |

FOREIGN PATENT DOCUMENTS 547130 3/1932 Fed. Rep. of Germany ........ 239/44

Primary Examiner—Richard D. Lovering
Attorney, Agent, or Firm—Armstrong, Nikaido, Marmelstein & Kubovcik

[57] ABSTRACT

The invention provides a method of vaporizing and a device capable of thermally vaporizing a thermally vaporizable composition being drawn up by a porous absorbing body due to its capillary attraction.

32 Claims, 5 Drawing Figures

DEVICE AND METHOD FOR VAPORIZING THERMALLY VAPORIZABLE COMPOSITION

This application is a division of application Ser. No. 639,299 filed Aug. 10, 1984, and now abandoned.

TECHNICAL FIELD

This invention relates to thermally vaporizable compositions and more particularly to improved compositions suitable for use in a device capable of thermally vaporizing the vaporizable composition being drawn up by a porous absorbing body due to its capillary attraction (the body will be referred to as "absorbing body" throughout the specification and appended claims).

BACKGROUND ART

It has been widely practiced to vaporize an active ingredient such as insecticide, perfume, etc. by heating a composition which contains the same and which is adsorbed on a mat, fiber plate or like porous substrate with the use of a heating device such as an electric mosquito-destroying device. However, this method involves the use of a mat impregnated with an inevitably limited amount of the active ingredient and requires replacement and disposal of the mat after use. The method also has the serious drawback of the the fugacity rate of active ingredient being reduced with the lapse of time. Further, the method is disadvantageous in that an effective volatilization ratio is as low as about 50%, permitting about 10% of the active ingredient to remain in the substrate and failing to retain a stable fumigating effect over a prolonged period of time. For these reasons, the method entails great economical disadvantages.

In order to overcome the problems of replacing waste mats and the loss of the fumigating effect in a short period of time, an improved method capable of maintaining the desired effect for a prolonged period of time has been proposed. The improved method involves the thermal vaporization of a solution of active ingredient being drawn up by an absorbing body. The proposal provides a device comprising a container for a solvent solution of active ingredient, an absorbing body of felt or like material for absorbing the solution and a heating means for heating the absorbing body so that the solution is volatilized off the top of the absorbing body (a device of this type will be referred to as "absorbing-vaporization device" throughout the specification and claims). However, when any of the absorbing-vaporization devices is operated in practice, the heating of the absorbing body causes the solvent in the solution to preferentially vaporize, thereby gradually concentrating the solution within the absorbing body. This is likely to form resinous solids in the body and to carbonize the same. Such phenomena give rise to clogging in the absorbing body, whereby subsequent absorption and volatilization of the solution are inhibited. This inhibition results in failure to retain the desired fumigating effect over a prolonged period of time, decrease in the desired effect with the passage of time, and reduction in the effective volatilization ratio, with a significant portion of the active ingredient being left unused. The causes for these problems attendant on the foregoing method may be attributed to various factors. These factors include the selection of an absorbing body, solvent and active ingredient, the concentration of the active ingredient, heating conditions, etc. The problems have been difficult to solve.

OBJECTS OF INVENTION

It is an object of the present invention to provide thermally vaporizable compositions for use in an absorbing body suitable for absorbing-vaporization devices.

It is another object of the invention to provide an improved vaporizable composition which, when used in the foregoing devices, is able to keep the absorbing body from clogging and like drawbacks, and is able to maintain a high desired effect over a prolonged period of time, which results in vaporization of the active ingredient in an increased amount and achieves a higher effective volatilization ratio.

DISCLOSURE OF INVENTION

This invention provides a thermally vaporizable composition suited for an absorbing body which comprises an organic solvent, an active ingredient and at least one compound selected from the group consisting of: 3,5-di-t-butyl-4-hydroxytoluene, 3-t-butyl-4-hydroxyanisole, 3,5-di-t-butyl-4-hydroxyanisole, mercaptobenzimidazole, dilauryl-thio-di-propionate, 2-t-butyl-4-methoxyphenol, 3-t-butyl-4-methoxyphenol, 2,6-di-t-butyl-4-ethylphenol, stearyl-$\beta$-(3,5-di-t-butyl-4-hydroxyphenyl)propionate, $\alpha$-tocopherol, ascorbic acid, erythorbic acid, 2,2'-methylene-bis(6-t-butyl-4-methylphenol), 2,2'-methylene-bis(6-t-butyl-4-ethylphenol), 4,4'-methylene-bis(2,6-di-t-butylphenol), 4,4'-butylidene-bis(6-t-butyl-3-methylphenol), 4,4'-thio-bis(6-t-butyl-3-methylphenol), 1,1-bis(4-hydroxyphenyl)cyclohexane, 1,3,5-trimethyl-2,4,6-tris(3,5-di-t-butyl-4-hydroxybenzyl)benzene, tris(2-methyl-4-hydroxy-5-t-butylphenyl)butane, tetrakis[methylene(3,5-di-t-butyl-4-hydroxyhydrocinnamate)]methane, octadecyl-3,5-di-t-butyl-4hydroxyhydrocinnamate, phenyl-$\beta$-naphthylamine, N,N-diphenyl-p-phenylenediamine, 2,2,4-trimethyl-1,3-dihydroquinoline polymer and 6-ethoxy-2,2,4-trimethyl-1,3-dihydroquinoline.

The thermally vaporizable composition of the present invention, when used in the absorbing-vaporization device, enables the absorbing body to function without clogging and serves to extend the life of the absorbing body so that the active ingredient can be volatilized with an appreciable increase in efficiency (namely in a markedly larger amount and at a significantly higher effective volatilization ratio) and a sustained high fumigating effect can be achieved over a prolonged period of time.

The active ingredients useful in this invention are diverse and include those heretofore used for insecticidal, fungicidal, incensing and other purposes. Typical useful examples are as follows.

1. Insecticide

The insecticides useful in the present invention can be any of those heretofore commonly used to control vermin and including a variety of pyrethroid-type insecticides, carbamate-type insecticides and organic phosphorus-type insecticides.

(1) 3-Allyl-2-methylcyclopenta-2-ene-4-one-1-yl dl-cis/trans-chrysanthemate (generally called allethrin, available under the trademark "Pynamin", product of SUMITOMO CHEMICAL CO., LTD., Japan, hereinafter referred to as "AA");

(2) 3-Allyl-2-methylcyclopenta-2-ene-4-one-1-yl d-cis/trans-chrysanthemate (available under the trade mark "Pynamin-forte", product of SUMITOMO CHEMICAL CO., LTD., Japan, hereinafter referred to as "AB");

(3) d-3-Allyl-2-methylcyclopenta-2-ene-4-one-1-yl d-trans-chrysanthemate (available under the trademark "Extrin", product of SUMITOMO CHEMICAL CO., LTD., Japan, hereinafter referred to as "AC");

(4) 3-Allyl-2-methylcyclopenta-2-ene-4-one-1-yl d-trans-chrysanthemate (generally called bioallethrin, hereinafter referred to as "AD");

(5) N-(3,4,5,6-Tetrahydrophthalimide)-methyl dl-cis/-transchrysanthemate (generally called phthalthrin, available under the trademark "Neo-pynamin", product of SUMITOMO CHEMICAL CO., LTD., Japan, hereinafter referred to as "AE");

(6) 5-Benzyl-3-furylmethyl d-cis/trans-chrysanthemate (generally called resmethrin, available under the trademark "Chrysron-forte", product of SUMITOMO CHEMICAL CO., LTD., Japan, hereinafter referred to as "AF");

(7) 5-(2-Propargyl)-3-furylmethyl chrysanthemate (generally called furamethrin, hereinafter referred to as "AG");

(8) 3-Phenoxybenzyl 2,2-dimethyl-3-(2',2'-dichloro)-vinylcyclopropane carboxylate (generally called permethrin, available under the trademark "Exmin", product of SUMITOMO CHEMICAL CO., LTD., Japan, hereinafter referred to as "AH");

(9) 3-Phenoxybenzyl d-cis/trans-chrysanthemate (generally called phenothrin, available under the trademark "Sumithrin", product of SUMITOMO CHEMICAL CO., LTD., Japan, hereinafter referred to as "AI";

(10) α-Cyanophenoxybenzyl isopropyl-4-chlorophenyl acetate (generally called fenvalerate, available under the trademark "Sumicidin", product of SUMITOMO CHEMICAL CO., LTD., Japan, hereinafter referred to as "AJ");

(11) d-3-Allyl-2-methylcyclopenta-2-ene-4-one-1-yl d-trans-chrysanthemate (available under the trademark "Exrin", product of SUMITOMO CHEMICAL CO., LTD., Japan, hereinafter referred to as "AK");

(12) (S)-α-Cyano-3-phenoxybenzyl (1R, cis)-3-(2,2-dichlorovinyl)-2,2-dimethylcyclopropanecarboxylate (hereinafter referred to as "AL");

(13) (R,S)-α-Cyano-3-phenoxybenzyl (1R, 1S)-cis/-trans-3-(2,2-dichlorovinyl)-2,2-dimethylcyclo-propanecarboxylate (hereinafter referred to as "AM");

(14) α-Cyano-3-phenoxybenzyl d-cis/trans-chrysanthemate (hereinafter referred to as "AN");

(15) 1-Ethynyl-2-methyl-2-pentenyl cis/trans-chrysanthemate (hereinafter referred to as "AO");

(16) 1-Ethynyl-2-methyl-2-pentenyl 2,2-dimethyl-3-(2-methyl-1-propenyl)cyclopropane-1-carboxylate (hereinafter referred to as "AP");

(17) 1-Ethynyl-2-methyl-2-pentenyl 2,2,3,3-tetramethylcyclopropanecarboxylate (hereinafter referred to as "AQ");

(18) 1-Ethynyl-2-methyl-2-pentenyl 2,2-dimethyl-3-(2,2-dichlorovinyl)cyclopropane-1-carboxylate (hereinafter referred to as "AR");

(19) O,O-Dimethyl O-(2,2-dichloro)vinylphosphate (hereinafter referred to as "AS");

(20) o-Isopropoxyphenyl methylcarbamate (hereinafter referred to as "AT");

(21) O,O-Dimethyl O-(3-methyl-4-nitrophenyl)thiophosphate (hereinafter referred to as "AU");

(22) O,O-Diethyl O-2-isopropyl-4-methyl-pyrimidyl-(6)-thiophosphate;

(23) O,O-Dimethyl S-(1,2-dicarboethoxyethyl)dithiophosphate; etc.

2. Deodorant

Lauryl methacrylate, geranyl crotonate, acetophenone myristate, p-methyl acetophenone benzaldehyde, benzyl acetate, benzyl propionate, amylcinnamic aldehyde, anisic aldehyde, diphenyl oxide, methyl benzoate, ethyl benzoate, methyl phenylacetate, ethyl phenylacetate, neoline, safrole, etc.

3. Natural perfume

Musk, civet, ambergis, castoreum and like animal perfumes; abies oil, ajowan oil, almond oil, ambrette seed absolute, angelic root oil, anise oil, basil oil, bay oil, benzoin resinoid, bergamot oil, birch oil, bois de rose oil, broom abs., cajeput oil, cananga oil, capsicum oil, caraway oil, cardamon oil, carrot seed oil, cassia oil, cedarwood oil, celery seed oil, cinnamon bark oil, citronella oil, clary sage oil, clove oil, cognac oil, coriander oil, cubeb oil, cumin oil, camphor oil, dill oil, estragon oil, eucalyptus oil, fennel sweet oil, galbanum res., garlic oil, geranium oil, ginger oil, grapefruit oil, hop oil, hyacinth abs., jasmin abs., juniper berry oil, labdanum res., lavandin oil, laurel leaf oil, lavender oil, lemon oil, lemongrass oil, lime oil, lovage oil, mace oil, mandarin oil, mimosa abs., myrrh abs., mustard oil, narcissus abs., neroli bigarade oil, nutmeg oil, oakmoss abs., olibanum res., onion oil, opoponax res., orange oil, orange flower oil, orris concrete, pepper oil, peppermint oil, peru balsam, petitgrain oil, pine needle oil, rose abs., rose oil, rosemary oil, sandalwood oil, sage oil, spearmint oil, styrax oil, thyme oil, tolu balsam, tonka beans abs., tuberose abs., turpentine oil, vanilla beans abs., vetiver oil, violet leaf abs., ylang ylang oil and like vegetable oils, etc.

4. Artificial perfume (synthetic or extract oil)

Pinene, limonene and like hydrocarbons; 3,3,5-trimethylcyclohexanol, linalool, geraniol, nerol, citronellol, menthol, borneol, borneyl methoxy cyclohexanol, benzyl alcohol, anise alcohol, cinnamyl alcohol, β-phenyl ethyl alcohol, cis-3-hexenol, terpineol and like alcohols; anethole, musk xylol, isoeugenol, methyl eugenol and like phenols; α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, citral, citronellal, hydroxycitronellal, benzaldehyde, methyl nonyl acetaldehyde, cinnamic aldehyde, dodecanol, α-hyxylcinnamic aldehyde, undecenal, heliotropin, vanillin, ethyl vanillin and like aldehydes; methyl amyl ketone, methyl β-naphthyl ketone, methyl nonyl ketone, musk ketone, diacetyl, acetyl propionyl, acetyl butyryl, carvone, menthone, camphor, acetophenone, p-methyl acetophenone, ionone, methyl ionone and like ketones; amyl butyrolactone, diphenyl oxide, methyl phenyl glycidate, γ-nonyl lactone, coumarin, cineole, ethyl methyl phenyl glicydate and like lactones or oxides; methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, methyl salicylate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, nopyl acetate, β-phenylethyl acetate, trichloromethylphenyl carbinyl acetate, terpinyl acetate, vetiveryl acetate and like esters.

These perfumres can be used singly or at least two of them are usable in admixture.

When required, the composition of the present invention can contain, in addition to perfume, additives commonly used in perfume industry, such as patchouli oil or a similar volatility inhibitor, eugenol or a similar viscosity-adjusting agent.

5. Industrial bactericide and fungicide 2,4,4'-Trichoro-2'-hydroxydiphenyl ether, 2,3,5,6-tetrachloro-4(methylsulfonyl)pyridine, alkylbenzyl dimethyl ammonium chloride, benzyldimethyl[2-[2-(p-1,1,3,3,-tetramethyl butylphenoxy)ethoxy]ethyl]ammonium chloride, 4-isopropyltropolone, N-dimethyl-N-phenyl-N'-(fluorodichloromethylthio)sulfone amide, 2-(4'-thiazolyl)benzimidazole, N-(fluorodichloromethylthio)-phthalimide, 6-acetoxy-2,4-dimethyl-m-dioxine, etc.

6. Agricultural bactericide and fungicide

Zinc ethylene bisdithiocarbamate, maganese ethylene bisdithiocarbamate, complex of zinc and maneb, bisdimethyl dithiocarbamoyl zinc ethylene bisdithiocarbamate, bis(dimethylthiocarbamoyl)disulfide, isomer of crotonic acid and 2,6-dinitro-4-octylphenyl, etc.

7. Vermin repellent

Dimethylphthalate, 2,3,4,5-bis-($\Delta_2$-butylene)-tetrahydrofuran, 2,3,4,5-bis-($\Delta_2$-butylene)-tetrahydrofurfuryl alcohol, N,N-diethyl-m-toluamide (hereinafter referred to "DET"), caprylic acid diethylamide, 2,3,4,5-bis-($\Delta_2$-butylene)tetrahydrofurfural, di-n-propylisocinchomeronate, secondary butyl styryl ketone, nonyl styryl ketone, N-propyl acetanilide, 2-ethyl-1,3-hexane diol, di-n-butyl succinate, 2-butoxyethyl-2-furfurylidene acetate, dibutyl phthalate, tetrahydrothiophene, β-naphthol, diallyl disulfide, bis(dimethylthiocarbamoyl)disulfide, etc.

8. Rodent repellent

Tetramethylthiuram disulfite, guanidine, naphthalene creosol, cycloheximide, zinc dimethyl dithiocarbamate, cyclohexyl amine, N,N-dimethylsulphenyl dithiocarbamate, etc.

9. Dog and cat repellent 2,6-Dimethyl-octadiene-(2,6)-al(8) (hereinafter referred to as "citral") O,O-diethyl S-2-ethylthioethyl dithiophosphate (hereinafter referred to as "ETP"), O,O-dimethyl S-2-isopropyl thioethyl dithiophosphate (hereinafter referred to as "MIP"), etc.

10. Bird repellent

Chloralose, 4-(methylthio)-3,5-xylyl-N-methylcarbamate, 4-aminopyridine anthraquinone, tetramethylthiuram disulfite, diallyl disulfide, etc.

11. Rodenticide

ANTU, sodium monofluoro acetate, warfarin, coumachlor, fumarine, norbomide, N-3-pyridylmethyl-N'-nitrophenylurea, α-naphthylthiourea, thiosemicarbazide, difenacoum, pival, chlorphacinone, carciferol, etc.

12. Formicide

Permethrin, chlorden, etc.

The active ingredient can be used cojointly with any of synergists, fugacity rate improving agents, etc. which are used in conventional fumigating composition. Preferably examples of the synergists are piperonyl butoxide, N-propyl isome, "MGK-264" (product of MCLAUGHLIN GORMLEY KING CO., U.S.A.), "Cynepirin-222" (product of YOSHITOMI PHARMACEUTICAL INDUSTRIES LTD., Japan), "Cynepirin-500" (product of YOSHITOMI PHARMACEUTICAL INDUSTRIES LTD., Japan), "Lethane 384" (product of ROHM AND HAAS COMPANY, U.S.A.), "IBTA" (product of NIPPON FINE CHEMICAL CO., LTD., Japan), "S-421" (product of SANYO CHEMICAL INDUSTRIES, LTD., Japan). Preferable fugacity rate improving agents include phenethylisothiocyanate, dimethylester of himic acid, etc.

At least one of the active ingredients exemplified above is formulated into a solution, according to the present invention. Solvents usable for preparing the solution can be any of suitable organic solvents, such as hydrocarbons. Preferred solvents are saturated and unsaturated aliphatic hydrocarbons having a boiling point in the range of about 150° to about 350° C. Among them, n-paraffin, isoparaffin and the like are more preferable since they are nontoxic, odorless and substantially free from fire hazards when put to use. Useful organic solvents other than the hydrocarbon-type solvents are glycerin, propylene glycol, methanol, acetone, benzene, xylene, chlorosen, isopropanol, solvent naphtha, methyl naphthalene, aromatic naphtha, chloroform, etc.

The concentration of active ingredient in the composition is usually in the range of about 1 to about 10% by weight, preferably in the range of about 3 to about 8% by weight.

The thermally vaporizable composition of the present invention contains at least one compound selected from the group consisting of:

(i) 3,5-di-t-butyl-4-hydroxytoluene (hereinafter referred to as "CA");

(ii) 3-t-butyl-4-hydroxyanisole (hereinafter referred to as "CB");

(iii) 3,5-di-t-butyl-4-hydroxyanisole (hereinafter referred to as "CC");

(iv) mercaptobenzimidazole (hereinafter referred to as "CD");

(v) dilauryl-thio-di-propionate (hereinafter referred to as "CE");

(vi) 2,2'-methylene-bis-(6-t-butyl-4-methylphenol) (hereinafter referred to as "CF");

(vii) 2,2'-methylene-bis-(6-t-butyl-4-ethylphenol) (hereinafter referred ot as "CG");

(viii) 4,4'-methylene-bis-(2,6-di-t-butylphenol) (hereinafter referred to as "CH");

(ix) 4,4'-butylidene-bis-(6-t-butyl-3-methylphenol) (hereinafter referred to as "CI");

(x) 4,4'-thio-bis-(6-t-butyl-3-methylphenol) (hereinafter referred to as "CJ");

(xi) 1,1-bis-(4-hydroxyphenyl)cyclohexane (hereinafter referred to as "CK");

(xii) 1,3,5-trimethyl-2,4,6-tris(3,5-di-t-butyl-4-hydroxybenzyl)benzene (hereinafter referred to as "CL");

(xiii) tris(2-methyl-4-hydroxy-5-t-butylphenyl)butane (hereinafter referred to as "CM");

(xiv) tetrakis[methylene(3,5-di-t-butyl-4-hydroxyhydrocinnamate)]methane (hereinafter referred to as "CN");
(xv) octadecyl-3,5-di-t-butyl-4-hydroxyhydrocinnamate (hereinafter referred to as "CO");
(xvi) phenyl-β2-naphthylamine (hereinafter referred to as "CP");
(xvii) N,N'-diphenyl-p-phenylenediamine (hereinafter referred to as "CQ");
(xviii) 2,2,4-trimethyl-1,3-dihydroquinoline polymer (hereinafter referred to as "CR");
(xix) 6-ethoxy-2,2,4-trimethyl-1,3-dihydroquinoline (hereinafter referred to as "CS");
(xx) 2-t-butyl-4-methyoxyphenol (hereinafter referred to as "CT");
(xxi) 3-t-butyl-4-methoxyphenol (hereinafter referred to as "CU");
(xxii) 2,6-di-t-butyl-4-ethylphenol (hereinafter referred to as "CW");
(xxiii) stearyl-$\beta$-(3,5-di-t-butyl-4-hydroxyphenyl)propionate (hereinafter referred to as "CW");
(xxiv) α-tocopherol (hereinafter referred to as "CX");
(xxv) ascorbic acid (hereinafter referred to as "CY"); and
(xxvi) erythorbic acid (hereinafter referred to as "CZ").

The compounds CA to CZ can be used singly or at least two of them are usable in admixture. The amount of the compound to be used is about 0.2 to about 1.0% by weight, preferably about 0.3 to about 0.9% by weight, based on the composition of the present invention.

The vaporizable composition of the present invention when charged into any of the conventional absorbing-vaporization devices can produce a high fumigating effect as contemplated. The devices of this type are disclosed, for example, in Japanese Examined Patent Publication No. 12106/1977 and Japanese Unexamined Patent Publication No. 45670/1983. Examples of the devices are shown in the attached drawings.

BRIEF DESCRIPTION OF THE DRAWINGS

FIG. 1 is a schematic view showing an absorbing-vaporization device for the vaporization of the present composition. Referring to FIG. 1, the device comprises an absorbing body; a support member 2 for holding the absorbing body 1; a container 3 for the vaporization composition, the container 3 having the support member 2 and the absorbing body 1 with its upper portion projecting from the container 3; a ring-shaped heating member 4 for indirectly heating the upper portion of the absorbing body 1; a receptacle 5 for accommodating the heating member 4; a support frame 6; and a base 7 from which the support frame 6 extends upward to support the receptacle 5. The heater 4 has unillustrated wires which connect the heater to an energy source (not shown).

Figure 1:
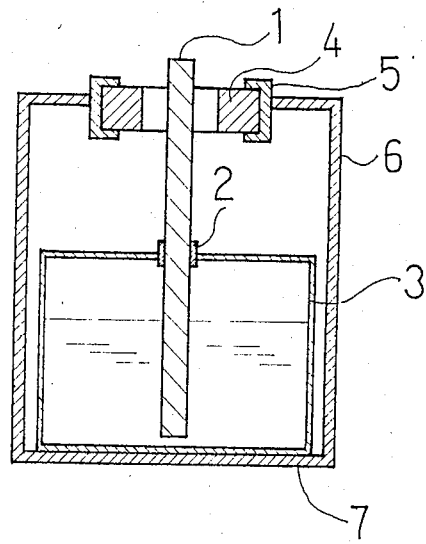
FIG. 1 schematically illustrates an absorbing vaporization device.

The absorbing body 1 can be made of any appropriate absorbing materials commonly used in the art such as felt, cotton, non-woven fabric, asbestos, inorganic shaped bodies, etc. Preferred absorbing bodies are those of felt, biscuit, pulp and inorganic shaped bodies. Examples of suitable inorganic shaped bodies are those molded from particles of porous porcelain or glass fiber, asbestos or like inorganic fibers which are held together with gypsum, bentonite or like binder or those formed from particles of kaolin, activated clay, talc, diatomaceous earth, clay, perlite, bentonite, alumina, silica, alumina-silica or titanium, virtreous particles of baked volcanic rock or volcanic ash or like particles of mineral materials which are used singly or in admixture with particles of wood, charcoal, active carbon or the like, the whole particles being bonded together with dextrin, starch, gum arabic, synthetic adhesive, carboxylmethyl cellulose or like binder. Preferred absorbing bodies are produced by mixing 100 parts by weight of at least one of the above-exemplified powdery mineral materials with 10 to 300 parts by weight of, powdery wood or, a mixture of powdery wood and powdery charcoal and/or active carbon in an amount equal to or less than that of the powdery wood; adding to the mixture 5 to 25% by weight of a binder based on the weight of the absorbing body and then water; kneading the mixture; molding the resulting mass by extrusion; and drying the molded piece. When required, suitable additives can be incorporated into the above mixture of powdery mineral material, wood particles and binder. Useful additives include Malachite Green and like coloring agents, sorbic acid and its salt, dehydroacetic acid and like fungicides, etc.

The absorbing body has an oil absorption rate of preferably 1 to 40 hours, more preferably 8 to 21 hours. The term oil absorption rate used herein refers to the value which is given by determining the time for n-paraffin to reach the upper end of the absorbing body 7 mm in diameter and 70 mm in length immersed at 25° C. in n-paraffin to a depth of 15 mm as measured from the lower end of the body.

Widely used as the heating means for the conventional absorbing-vaporization devices are those which emit heat when electrically energized. The heating means usable for heating the present compositions are not limited to such electric heaters but can be any of appropriate heating means or heat sources such as a material which gives off heat when reacted with oxygen, and a heating material using platinum or like catalyst.

Figure 2:
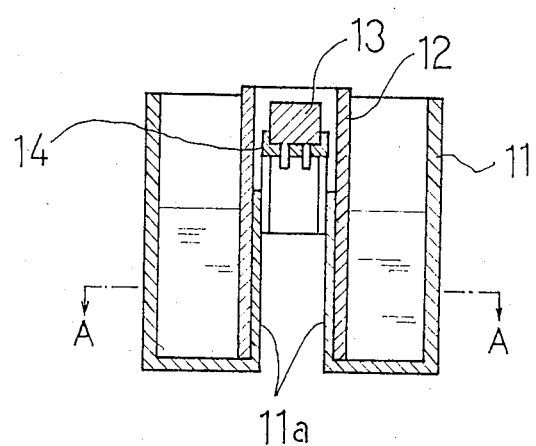
FIG. 2 schematically illustrates an absorbing vaporization device in longitudinal section.
Figure 3:
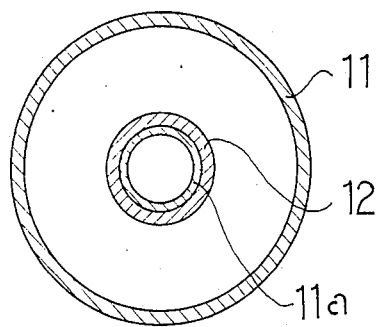
FIG. 3 is a cross-sectional schematic illustration of an absorbing-vaporization device.

FIG. 2 is a longitudinal section schematically showing another example of an absorbing-vaporization device suitable for vaporization of the present composition. FIG. 3 is a cross-sectional view of the device taken on line A—A in FIG. 2. The illustrated device comprises a double-cylinder type container 11 for accommodating the composition, an absorbing body 12 disposed in the container 11 and arranged in contact with a central cylinder 11a, a heating means 13 for indirectly heating the upper portion of the absorbing body 12 and a supporting member 14 for supporting the heater means 13. The heating means 13 is provided with unillustrated wires for electrical energization of the means 13.

Figure 4:
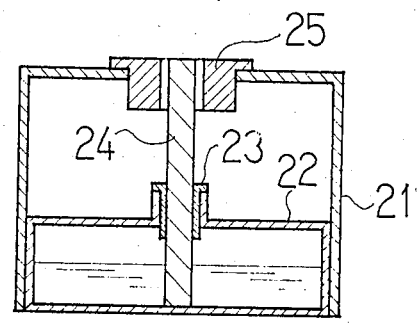
FIG. 4 schematically illustrates another absorbing-vaporization device in longitudinal section.
Figure 5:
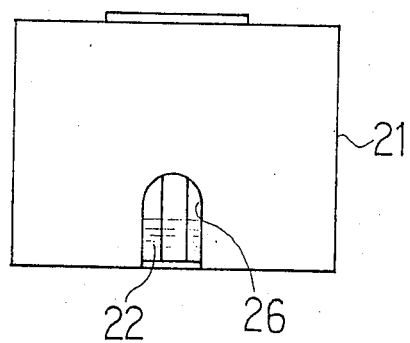
FIG. 5 illustrates the device of FIG. 4 showing a cut out in the container.

FIG. 4 is a longitudinal section schematically showing a further example of an absorbing-vaporization device suited to evaporation of the present composition. The device includes a frame 21, a container 22 for accommodating the composition which container is in contact with the frame 21, an absorbing body 24, a supporting member 23 for supporting the absorbing body 24 and a heating means 25 mounted to an opening in the upper portion of the frame 21. The container 22 indirectly supports the absorbing body 24 through the supporting member 23. In operation, the heating means 25 is electrically energized by unillustrated wires to indirectly heat the upper portion of the absorbing body 24, whereby the composition is vaporized in the same manner as in operation of the device shown in FIG. 1. If the device depicted in FIG. 4 has a cutout 26 in the frame 21 as indicated in FIG. 5, the container 22 can be easily inserted into and removed from the frame 21. If the container 22 is made of a transparent material, the amount of the composition portion remaining in the container 22 can be conveniently detected through the cutout 26.

The absorbing-vaporization device provided with the present vaporizable composition can effectively vaporize the composition by the same process as the conventional devices of this type in which the absorbing body is heated to a temperature adequate to vaporize the composition off the body. The heating temperature is suitably determined, depending on the kind of the active ingredient, etc. and is not particularly limited. The surface of the heater is heated to usually about 40° to about 150° C., preferably about 85° to about 145° C. by which the surface of the absorbing body is correspondingly heated to usually about 30° to about 135° C., preferably about 70° to about 130° C.

The vaporizable composition of the present invention which incorporates therein at least one of the compounds CA–CZ prevents the clogging in the absorbing body and can achieve continuous vaporization of the composition over a prolonged period of time while maintaining an adequate active ingredient concentration to produce a high fumigating effect.

The present invention will be described below in more detail with reference to the following Examples and Comparison Examples.

EXAMPLES 1 TO 64

Samples of the insecticidal compositions according to the present invention were prepared by mixing the insecticides AA to AU, organic solvents and compounds CA to CZ in the proportions as shown in Table 1 below.

COMPARISON EXAMPLES 1 TO 14

Samples of insecticial compositions for comparison were prepared in the same manner as Examples 1 to 64 with the exception of not using the compounds CA to CZ.

TABLE 1

| | Insecticide (wt %) | Compound (wt %) | Solvent (wt %) | |
|---|---|---|---|---|
| Example No. | | | | |
| 1 | AA (4) | CA (0.3) | BC | (95.7) |
| 2 | AA (4) | CB (0.3) | BD | (95.7) |
| 3 | AA (4) | CC (0.3) | BE | (95.7) |
| 4 | AA (4) | CF (0.3) | BA/BF | (95.7) |
| 5 | AA (4) | CI (0.3) | BB/BE | (95.7) |
| 6 | AA (4) | CQ (0.3) | BC/BD | (95.7) |
| 7 | AA (6) | CA (0.3) | BC | (93.7) |
| 8 | AA (6) | CA (0.5) | BD | (93.5) |
| 9 | AA (8) | CB (0.3) | BE | (91.7) |
| 10 | AA (8) | CB (0.5) | BB/BD | (91.5) |
| 11 | AB (4) | CA (0.3) | BA | (95.7) |
| 12 | AB (4) | CB (0.3) | BB | (95.7) |
| 13 | AB (4) | CC (0.3) | BC | (95.7) |
| 14 | AB (4) | CF (0.3) | BD | (95.7) |
| 15 | AB (4) | CI (0.3) | BE | (95.7) |

TABLE 1-continued

| | Insecticide (wt %) | Compound (wt %) | Solvent (wt %) | |
|---|---|---|---|---|
| 16 | AB (4) | CQ (0.3) | BF | (95.7) |
| 17 | AB (4) | CA (0.6) | BB | (95.4) |
| 18 | AB (4) | CB (0.6) | BC | (95.4) |
| 19 | AB (4) | CC (0.6) | BD | (95.4) |
| 20 | AB (6) | CA (0.3) | BD | (93.7) |
| 21 | AB (6) | CB (0.3) | BD | (93.7) |
| 22 | AB (6) | CC (0.3) | BD | (93.7) |
| 23 | AB (6) | CF (0.6) | BD | (93.4) |
| 24 | AB (6) | CI (0.6) | BD | (93.4) |
| 25 | AB (6) | CQ (0.6) | BD | (93.4) |
| 26 | AB (8) | CA (0.3) | BC | (91.7) |
| 27 | AB (8) | CB (0.3) | BD | (91.7) |
| 28 | AB (8) | CA (0.9) | BA/BF | (91.1) |
| 29 | AB (8) | CB (0.9) | BB/BE | (91.1) |
| 30 | AD (4) | CA (0.3) | BD | (95.7) |
| 31 | AD (4) | CB (0.3) | BD | (95.7) |
| 32 | AD (4) | CC (0.6) | BC | (95.4) |
| 33 | AD (4) | CF (0.6) | BC | (95.4) |
| 34 | AD (8) | CI (0.3) | BA/BD | (91.7) |
| 35 | AD (8) | CQ (0.6) | BB/BE | (91.4) |
| 36 | AF (4) | CA (0.3) | BB | (95.7) |
| 37 | AF (4) | CB (0.6) | BC | (95.4) |
| 38 | AF (8) | CC (0.3) | BD | (91.7) |
| 39 | AF (8) | CF (0.9) | BE | (91.1) |
| 40 | AG (4) | CA (0.3) | BB | (95.7) |
| 41 | AG (4) | CB (0.3) | BC | (95.7) |
| 42 | AG (4) | CC (0.6) | BD | (95.4) |
| 43 | AG (4) | CF (0.6) | BE | (95.4) |
| 44 | AG (8) | CI (0.3) | BA/BE | (91.7) |
| 45 | AG (8) | CQ (0.9) | BA/BE | (91.1) |
| 46 | AH (4) | CA (0.6) | BE | (95.4) |
| 47 | AI (4) | CA (0.6) | BE | (95.4) |
| 48 | AO (4) | CA (0.3) | BB | (95.7) |
| 49 | AP (4) | CA (0.3) | BA | (95.7) |
| 50 | AP (4) | CB (0.6) | BB | (95.4) |
| 51 | AP (6) | CC (0.3) | BC | (93.7) |
| 52 | AP (6) | CF (0.6) | BD | (93.4) |
| 53 | AP (8) | CI (0.3) | BA/BC | (91.7) |
| 54 | AP (8) | CQ (0.6) | BA/BC | (91.4) |
| 55 | AQ (4) | CA (0.3) | BB | (95.7) |
| 56 | AQ (4) | CB (0.3) | BC | (95.7) |
| 57 | AQ (6) | CC (0.6) | BD | (93.4) |
| 58 | AQ (6) | CF (0.6) | BE | (93.4) |
| 59 | AQ (8) | CI (0.9) | BA/BD | (91.1) |
| 60 | AQ (8) | CQ (0.9) | BB/BC | (91.1) |
| 61 | AR (8) | CA (0.3) | BB | (91.7) |
| 62 | AS (8) | CB (0.3) | BC | (91.7) |
| 63 | AT (8) | CC (0.3) | BD | (91.7) |
| 64 | AU (6) | CA (0.6) | BB | (93.4) |
| Comparison Ex. No. | | | | |
| 1 | AA (4) | — | BC | (96) |
| 2 | AA (8) | — | BD | (92) |
| 3 | AB (4) | — | BC | (96) |
| 4 | AB (8) | — | BD | (92) |
| 5 | AD (4) | — | BB | (96) |
| 6 | AD (8) | — | BC | (92) |
| 7 | AF (4) | — | BD | (96) |
| 8 | AG (4) | — | BE | (96) |
| 9 | AH (4) | — | BD | (96) |
| 10 | AI (4) | — | BE | (96) |
| 11 | AO (4) | — | BB | (96) |
| 12 | AP (4) | — | BC | (96) |
| 13 | AQ (4) | — | BB | (96) |
| 14 | AS (4) | — | BC | (96) |

The letters BA to BF used in Table 1 denote aliphatic hydrocarbons having the properties as shown in Table 2.

TABLE 2

| | Boiling point | Specific gravity (15/4° C.) | Main ingredient |
|---|---|---|---|
| BA | 150–180° C. | 0.748 | n-Decane, n-Nonane |
| BB | 180–210° C. | 0.759 | n-Undecane |
| BC | 210–240° C. | 0.760 | n-Tridecane, n-Dodecane |

TABLE 2-continued

| | Boiling point | Specific gravity (15/4° C.) | Main ingredient |
|---|---|---|---|
| BD | 240-270° C. | 0.769 | n-Tetradecane |
| BE | 270-300° C. | 0.823 | iso-Pentadecane, n-Hexadecane |
| BF | 300-350° C. | 0.777 | n-Octadecane |

A 50 ml quantity of each of the present compositions obtained in Examples 1 to 64 and the compositions prepared in Comparison Examples 1 to 14 was placed in the container 3 as illustrated in FIG. 1. The heater 4 was electrically energized to heat the upper portion of the absorbing body 1 to 135° C. The samples were tested for the degree of volatilization which was achieved by the insecticide present in the composition heated by the heated absorbing body. The absorbing body 1 was produced by mixing 60 parts by weight of perlite, 20 parts by weight of powdery wood and 20 parts by weight of starch, followed by addition of water; kneading the mixture; shaping the resulting mass by extrusion; and drying the shaped body. The dried piece was 7 mm in diameter and 70 mm in length and had an oil absorption rate of about 14 hours. The heater was a ring-shaped plate 10 mm in inside diameter and 10 mm in thickness.

The amount of the vaporized insecticide was measured by hourly collecting the vapor into a silica gel column by suction, extracting the silica gel with chloroform, concentrating the extract and quantitatively analyzing the concentrate by gas chromatography.

Table 3 below indicates the amounts of the insecticides vaporized (mg/hr) which amounts were measured 10 hours, 100 hours, 200 hours, 300 hours and 400 hours, respectively after the initiation of heating.

TABLE 3

| Sample | Time passed after initiation of heating (hr) | | | | |
|---|---|---|---|---|---|
| | 10 | 100 | 200 | 300 | 400 |
| Ex. No. | | | | | |
| 1 | 3.51 | 3.73 | 3.62 | 3.48 | 3.29 |
| 2 | 3.39 | 3.68 | 3.68 | 3.51 | 3.36 |
| 3 | 3.47 | 3.80 | 3.61 | 3.42 | 3.20 |
| 4 | 3.55 | 3.60 | 3.49 | 3.27 | 3.17 |
| 5 | 3.43 | 3.70 | 3.56 | 3.29 | 3.08 |
| 6 | 3.53 | 3.73 | 3.60 | 3.35 | 3.19 |
| 7 | 5.04 | 5.48 | 5.42 | 5.08 | 4.99 |
| 8 | 5.18 | 5.59 | 5.51 | 5.20 | 5.06 |
| 9 | 6.69 | 7.28 | 7.20 | 7.01 | 6.50 |
| 10 | 6.91 | 7.38 | 7.27 | 7.00 | 6.48 |
| 11 | 3.59 | 3.84 | 3.78 | 3.63 | 3.48 |
| 12 | 3.60 | 3.72 | 3.77 | 3.58 | 3.55 |
| 13 | 3.42 | 3.68 | 3.70 | 3.51 | 3.39 |
| 14 | 3.56 | 3.77 | 3.81 | 3.64 | 3.52 |
| 15 | 3.44 | 3.73 | 3.76 | 3.63 | 3.46 |
| 16 | 3.47 | 3.88 | 3.55 | 3.47 | 3.27 |
| 17 | 3.51 | 3.86 | 3.79 | 3.60 | 3.63 |
| 18 | 3.64 | 3.79 | 3.80 | 3.68 | 3.62 |
| 19 | 3.50 | 3.83 | 3.68 | 3.70 | 3.48 |
| 20 | 5.17 | 5.60 | 5.58 | 5.27 | 5.06 |
| 21 | 5.26 | 5.77 | 5.72 | 5.38 | 5.21 |
| 22 | 5.36 | 5.62 | 5.58 | 5.39 | 5.13 |
| 23 | 5.23 | 5.68 | 5.69 | 5.42 | 5.08 |
| 24 | 5.31 | 5.72 | 5.72 | 5.59 | 5.26 |
| 25 | 5.18 | 5.69 | 5.66 | 5.48 | 5.39 |
| 26 | 7.00 | 7.48 | 7.28 | 7.06 | 6.52 |
| 27 | 6.95 | 7.43 | 7.51 | 7.26 | 6.62 |
| 28 | 7.11 | 7.53 | 7.62 | 7.25 | 6.93 |
| 29 | 7.20 | 7.47 | 7.53 | 7.33 | 6.85 |
| 30 | 3.50 | 3.78 | 3.62 | 3.51 | 3.36 |
| 31 | 3.50 | 3.62 | 3.67 | 3.50 | 3.35 |
| 32 | 3.48 | 3.71 | 3.69 | 3.56 | 3.37 |
| 33 | 3.52 | 3.69 | 3.68 | 3.54 | 3.47 |
| 34 | 6.92 | 7.48 | 7.55 | 7.23 | 6.72 |
| 35 | 7.38 | 7.62 | 7.57 | 7.46 | 6.94 |
| 36 | 3.48 | 3.72 | 3.50 | 3.13 | 2.74 |
| 37 | 3.50 | 3.67 | 3.61 | 3.20 | 2.96 |
| 38 | 7.01 | 7.36 | 7.28 | 6.78 | 6.26 |
| 39 | 7.18 | 7.49 | 7.56 | 6.99 | 6.62 |
| 40 | 3.47 | 3.68 | 3.71 | 3.35 | 3.22 |
| 41 | 3.40 | 3.52 | 3.67 | 3.20 | 3.05 |
| 42 | 3.51 | 3.64 | 3.41 | 3.34 | 3.16 |
| 43 | 3.48 | 3.71 | 3.37 | 3.30 | 3.23 |
| 44 | 6.87 | 7.27 | 7.31 | 6.97 | 6.44 |
| 45 | 6.95 | 7.45 | 7.50 | 7.14 | 6.76 |
| 46 | 3.42 | 3.53 | 3.42 | 3.05 | 2.97 |
| 47 | 3.38 | 3.62 | 3.49 | 3.23 | 3.00 |
| 48 | 3.48 | 3.79 | 3.68 | 3.62 | 3.47 |
| 49 | 3.44 | 3.78 | 3.60 | 3.53 | 3.40 |
| 50 | 3.51 | 3.91 | 3.83 | 3.62 | 3.57 |
| 51 | 5.23 | 5.45 | 5.57 | 5.52 | 5.39 |
| 52 | 5.33 | 5.70 | 5.54 | 5.66 | 5.40 |
| 53 | 7.01 | 7.54 | 7.38 | 7.24 | 7.08 |
| 54 | 7.23 | 7.68 | 7.50 | 7.37 | 7.21 |
| 55 | 3.41 | 3.68 | 3.52 | 3.36 | 3.40 |
| 56 | 3.37 | 3.51 | 3.62 | 3.28 | 3.20 |
| 57 | 5.20 | 5.49 | 5.53 | 5.26 | 5.30 |
| 58 | 5.26 | 5.67 | 5.43 | 5.62 | 5.37 |
| 59 | 7.08 | 7.62 | 7.41 | 7.28 | 7.23 |
| 60 | 7.16 | 7.53 | 7.47 | 7.38 | 7.10 |
| 61 | 6.94 | 7.26 | 7.39 | 7.06 | 6.88 |
| 62 | 7.21 | 7.43 | 7.21 | 7.36 | 7.06 |
| 63 | 6.97 | 7.36 | 7.35 | 7.06 | 6.64 |
| 64 | 7.08 | 7.47 | 7.31 | 6.99 | 6.43 |
| Comparison Ex. No. | | | | | |
| 1 | 3.26 | 3.01 | 1.75 | 0.53 | 0.12 |
| 2 | 6.57 | 5.83 | 2.29 | 0.01 | 0.0 |
| 3 | 3.38 | 3.16 | 1.92 | 0.89 | 0.27 |
| 4 | 6.82 | 6.01 | 2.55 | 0.10 | 0 |
| 5 | 3.08 | 3.12 | 2.01 | 0.85 | 0.19 |
| 6 | 6.60 | 5.98 | 2.34 | 0.06 | 0 |
| 7 | 3.00 | 2.46 | 1.17 | 0.13 | 0 |
| 8 | 3.18 | 3.02 | 1.84 | 0.37 | 0 |
| 9 | 3.22 | 2.67 | 1.27 | 0.48 | 0 |
| 10 | 3.28 | 2.79 | 1.33 | 0.62 | 0 |
| 11 | 3.47 | 3.03 | 2.24 | 0.97 | 0.32 |
| 12 | 3.56 | 3.40 | 2.41 | 1.28 | 0.46 |
| 13 | 3.35 | 3.18 | 2.66 | 1.07 | 0.28 |
| 14 | 3.71 | 3.38 | 2.06 | 0.98 | 0.23 |

Table 3 reveals that the insecticidal compositions of the present invention can vaporize the insecticide in a markedly increased amount without substantially reducing the vaporized amount 400 hours after the start of heating.

EXAMPLES 65 TO 96

Vaporizable compositions were prepared by using one of deodorants or perfumes (Examples 65 to 83) and bactericides or repellents (Examples 92 to 96), each of organic solvents and each of Compounds CA to CZ as shown below in Table 4.

The samples thus obtained were tested in the same manner as in Examples 1 to 64 for measuring the amounts of active ingredients released after the initiation of heating. Table 5 below shows the results.

TABLE 4

| Ex. No. | Active ingredient | Compound (wt %) | Solvent (wt %) | |
|---|---|---|---|---|
| 65 | Lauryl methacrylate (4) | CA (0.3) | BC | (95.7) |
| 66 | Lauryl methacrylate (8) | CA (0.6) | BD | (91.4) |
| 67 | Lauryl methacrylate (4) | CB (0.3) | BA/BD | (95.7) |
| 68 | Lauryl methacrylate (10) | CQ (0.9) | BB | (89.7) |
| 69 | Geranyl crotonate (4) | CA (0.3) | BC | (95.7) |
| 70 | Geranyl crotonate (8) | CA (0.6) | BD | (91.4) |
| 71 | Citronella oil (4) | CB (0.3) | BC | (95.7) |
| 72 | Pinene (4) | CA (0.3) | BA | (95.7) |

TABLE 4-continued

| Ex. No. | Active ingredient | Compound (wt %) | Solvent (wt %) | |
|---|---|---|---|---|
| 73 | Linalool (4) | CQ (0.3) | BB | (95.7) |
| 74 | Lianlool (10) | CA (0.3) | BC | (89.7) |
| 75 | Benzyl alcohol (4) | CB (0.6) | BD | (95.4) |
| 76 | Eugenol (8) | CQ (0.6) | BE | (91.4) |
| 77 | Citral (4) | CA (0.3) | BF | (95.7) |
| 78 | Citral (8) | CB (0.6) | BA/BD | (91.4) |
| 79 | Benzaldehyde (4) | CQ (0.3) | BB/BC | (95.7) |
| 80 | Camphor (10) | CA (0.9) | BB | (89.1) |
| 81 | Coumarin (8) | CB (0.6) | BC | (91.4) |
| 82 | Benzyl acetate (4) | CQ (0.3) | BA/BC | (95.7) |
| 83 | Ethyl myristate (4) | CA (0.3) | BB/BF | (95.7) |
| 84 | 2,4,4'-Trichloro-2'-hydroxydiphenyl ether (4) | CB (0.3) | BD | (95.7) |
| 85 | 2,4,4'-Trichloro-2'-hydroxydiphenyl ether (8) | CQ (0.6) | BD | (91.4) |
| 86 | 2,4,4'-Trichloro-2'-hydroxydiphenyl ether (10) | CA (0.9) | BD | (89.1) |
| 87 | Alkylbenzyl dimethyl ammonium chloride (4) | CA (0.3) | BB/BD | (95.7) |
| 88 | Alkylbenzyl dimethyl ammonium chloride (4) | CB (0.6) | BC | (95.7) |
| 89 | Alkylbenzyl dimethyl ammonium chloride (4) | CQ (0.3) | BC | (95.7) |
| 90 | Bis(dimethyl-thiocarbamoyl)-disulfide (2) | CA (0.3) | BD | (97.3) |
| 91 | Bis(dimethyl-thiocarbamoyl)-disulfide (4) | CA (0.6) | BD | (95.4) |
| 92 | N,N—diethyl-m-toluamide (4) | CQ (0.3) | BB | (95.7) |
| 93 | N,N—diethyl-m-toluamide (6) | CB (0.6) | BC | (93.4) |
| 94 | N,N—diethyl-m-toluamide (10) | CA (0.9) | BD | (89.1) |
| 95 | Cycloheximide (4) | CA (0.6) | BC | (95.4) |
| 96 | O,O—Dimethyl S—2-isopropylthioethyl dithiophosphate (4) | CA (0.6) | BC | (95.4) |

TABLE 5

| Ex. No. | Amount of released active ingredient (mg/hr) | | | | |
|---|---|---|---|---|---|
| | 10 Hr | 100 Hr | 200 Hr | 300 Hr | 400 Hr |
| 65 | 3.60 | 3.70 | 3.61 | 3.63 | 3.58 |
| 66 | 7.12 | 7.31 | 7.32 | 7.19 | 7.10 |
| 67 | 3.64 | 3.68 | 3.66 | 3.60 | 3.60 |
| 68 | 8.88 | 9.18 | 9.28 | 9.04 | 9.00 |
| 69 | 3.46 | 3.61 | 3.60 | 3.52 | 3.40 |
| 70 | 6.87 | 7.02 | 7.11 | 7.03 | 6.72 |
| 71 | 3.52 | 3.50 | 3.48 | 3.41 | 3.37 |
| 72 | 3.82 | 3.77 | 3.70 | 3.62 | 3.50 |
| 73 | 3.53 | 3.69 | 3.71 | 3.60 | 3.58 |
| 74 | 8.98 | 9.29 | 9.30 | 9.14 | 9.21 |
| 75 | 3.63 | 3.68 | 3.74 | 3.72 | 3.62 |
| 76 | 7.03 | 7.29 | 7.38 | 7.19 | 7.00 |
| 77 | 3.57 | 3.61 | 3.56 | 3.52 | 3.53 |
| 78 | 7.06 | 7.21 | 7.16 | 7.02 | 6.90 |
| 79 | 3.38 | 3.67 | 3.60 | 3.51 | 3.40 |
| 80 | 9.11 | 9.31 | 9.20 | 9.02 | 9.04 |
| 81 | 7.04 | 7.38 | 7.38 | 7.20 | 7.11 |
| 82 | 3.70 | 3.68 | 3.71 | 3.64 | 3.62 |
| 83 | 3.63 | 3.72 | 3.60 | 3.58 | 3.51 |
| 84 | 3.47 | 3.61 | 3.62 | 3.56 | 3.39 |
| 85 | 6.90 | 7.18 | 7.17 | 7.25 | 6.82 |
| 86 | 8.74 | 9.03 | 9.18 | 8.91 | 8.70 |
| 87 | 3.63 | 3.68 | 3.60 | 3.51 | 3.48 |
| 88 | 3.60 | 3.73 | 3.68 | 3.67 | 3.54 |
| 89 | 3.65 | 3.61 | 3.55 | 3.49 | 3.45 |
| 90 | 1.72 | 1.86 | 1.81 | 1.79 | 1.70 |
| 91 | 3.51 | 3.64 | 3.56 | 3.50 | 3.37 |
| 92 | 3.57 | 3.69 | 3.60 | 3.47 | 3.38 |
| 93 | 5.31 | 5.44 | 5.40 | 5.32 | 5.23 |
| 94 | 8.67 | 8.88 | 8.79 | 8.60 | 8.51 |
| 95 | 3.40 | 3.39 | 3.41 | 3.27 | 3.20 |

TABLE 5-continued

| Ex. No. | Amount of released active ingredient (mg/hr) | | | | |
|---|---|---|---|---|---|
| | 10 Hr | 100 Hr | 200 Hr | 300 Hr | 400 Hr |
| 96 | 3.54 | 3.69 | 3.57 | 3.50 | 3.40 |

What is claimed is:

1. A device for vaporizing a thermally vaporizable composition, the device comprising a container for accommodating the thermally vaporizable composition, an absorbing body disposed in the container with its upper portion projecting from the container and set in contact with the vaporizable compositions to draw up the vaporizable composition by capillary attraction and a heating means for indirectly heating the upper portion of the absorbing body, whereby the composition being drawn up through the absorbing body is volatilized off the heated upper portion of the absorbing body, the vaporizable composition comprising an organic solvent, an active ingredient and at least one compound selected from the group consisting of: 3,5-di-t-butyl-4-hydroxytoluene, 3-t-butyl-4-hydroxyanisole, mercaptobenzimidazole, dilauryl-thio-di-propionate, 2-t-butyl-4-methoxyphenol, 3-t-butyl-4-methoxyphenol, 2,6-di-t-butyl-4-ethylphenol, stearyl-β-(3,5-di-t-butyl-4-hydroxyphenyl)propionate, α-tocopherol, ascorbic acid, erythorbic acid, 2,2'-methylene-bis(6-t-butyl-4-methylphenol), 4,4'-methylene-bis(2,6-di-t-butyl-phenol), 4,4'-butylidene-bis(6-t-butyl-3-methylphenol), 4,4'-thio-bis(6-t-butyl-3-methylphenol), 1,1-bis(4-hydroxyphenyl)cyclohexane, 1,3,5-trimethyl-2,4,6-tris(3,5-di-t-butyl-4-hydroxybenzyl)benzene, tris(2-methyl-4-hydroxy-5-t-butylphenyl)butane, tetrakis[methylene(3,5-di-t-butyl-4-hydroxyhydrocinnamate)]methane, octadecyl-3,5-di-t-butyl-4-hydroxyhydrocinnamate, phenyl-β-naphthylamine, N,N-diphenyl-p-phenylenediamine, 2,2,4-trimethyl-1,3-dihydroquioline polymer and 6-ethoxy-2,2,4-trimethyl-1,3-dihydroquinoline, said composition comprising about 1% to about 10% by weight of the active ingredient and about 0.2 to about 1.0% by weight of the selected compound.

2. A device for vaporizing a thermally vaporizable composition as defined in claim 1 wherein the active ingredient is an insecticide.

3. A device for vaporizing a thermally vaporizable composition as defined in claim 1 wherein the active ingredient is a deodorant.

4. A device for vaporizing a thermally vaporizable composition as defined in claim 1 wherein the active ingredient is a natural perfume.

5. A device for vaporizing a thermally vaporizable composition as defined in claim 1 wherein the active ingredient is an artificial perfume.

6. A device for vaporizing a thermally vaporizable composition as defined in claim 1 wherein the active ingredient is an industrial bactericide or fungicide.

7. A device for vaporizing a thermally vaporizable composition as defined in claim 1 wherein the active ingredient is an agricultural bactericide or fungicide.

8. A device for vaporizing a thermally vaporizable composition as defined in claim 1 wherein the active ingredient is a vermin repellent.

9. A device for vaporizing a thermally vaporizable composition as defined in claim 1 wherein the active ingredient is a rodent repellent.

10. A device for vaporizing a thermally vaporizable composition as defined in claim 1 wherein the active ingredient is a dog and cat repellent.

11. A device for vaporizing a thermally vaporizable composition as defined in claim 1 wherein the active ingredient is a bird repellent.

12. A device for vaporizing a thermally vaporizable composition as defined in claim 1 wherein the active ingredient is a rodenticide.

13. A device for vaporizing a thermally vaporizable composition as defined in claim 1 wherein the active ingredient is a formicide.

14. A device for vaporizing a thermally vaporizable composition as defined in claim 1 wherein the solvent is at least one of aliphatic hydrocarbons having a boiling point in the range of about 150° to about 350° C.

15. A device for vaporizing a thermally vaporizable composition as defined in claim 1 wherein the solvent is at least one of glycerin, propylene glycol, methanol, acetone, benzene, xylene, chlorsen, isopropanol, solvent naphtha, methyl naphthalene, aromatic naphtha and chloroform.

16. A device for vaporizing a thermally vaporizable composition as defined in claim 1 wherein the composition comprises about 3 to about 8% by weight of the active ingredient and about 0.3 to about 0.9% by weight of the compound.

17. A method of vaporizing a thermally vaporizable composition comprising heating indirectly the upper portion of an absorbing body whereby the composition being drawn up through the absorbing body is volatilized off the heated upper portion of the absorbing body, said composition comprising an organic solvent, an active ingredient and at least one compound selected from the group consisting of: 3,5-di-t-butyl-4-hydroxytoluene, 3-t-butyl-4-hydroxy-anisole, mercaptobenzimidazole, dilauryl-thio-di-propionate, 2-t-butyl-4-methoxyphenol, 3-t-butyl-4-methoxyphenol, 2,6-di-t-butyl-4-ethylphenol, stearyl-$\beta$-(3,5-di-t-butyl-4-hydroxyphenyl)propionate, $\alpha$-tocopherol, ascorbic acid, erythorbic acid, 2,2'-methylene-bis(6-t-butyl-4-methylphenol), 4,4'-methylene-bis(2,6-di-t-butylphenol), 4,4'-butylidene-bis(6-t-butyl-3-methylphenol), 4,4'-thiobis(6-t-butyl-3-methylphenol), 1,1-bis(4-hydroxyphenyl)-cyclohexane, 1,3,5-trimethyl-2,4,6-tris(3,5-di-t-butyl-4-hydroxybenzyl)-benzene, tris(2-methyl-4-hydroxy-5-t-butyl-phenyl)butane, tetrakis[methylene(3,5-di-t-butyl-4-hydroxyhydrocinnamate)]methane, octadecyl-3,5-di-t-butyl-4-hydroxyhydrocinnamate, phenyl-$\beta$-naphtylamine, N,N-diphenyl-p-phenylenediamine, 2,2,4-trimethyl-3,3-dihydroquinoline polymer and 6-ethoxy-2,2,4-trimethyl-1,3-dihydroquinoline said composition comprising about 1% to about 10% by weight of the active ingredient and about 0.2 to about 1.0% by weight of the selected compound.

18. A method of vaporizing a thermally vaporizable composition as defined in claim 17, wherein the active ingredient is an insecticide.

19. A method of vaporizing a thermally vaporizable composition as defined in claim 17, wherein the active ingredient is a deodorant.

20. A method of vaporizing a thermally vaporizable composition as defined in claim 17, wherein the active ingredient is a natural perfume.

21. A method of vaporizing a thermally vaporizable composition as defined in claim 17, wherein the active ingredient is an artificial perfume.

22. A method of vaporizing a thermally vaporizable composition as defined in claim 17, wherein the active ingredient is an industrial bactericide or fungicide.

23. A method of vaporizing a thermally vaporizable composition as defined in claim 17, wherein the active ingredient is an agricultural bactericide or fungicide.

24. A method of vaporizing a thermally vaporizable composition as defined in claim 17, wherein the active ingredient is a vermin repellent.

25. A method of vaporizing a thermally vaporizable composition as defined in claim 17, wherein the active ingredient is a rodent repellent.

26. A method of vaporizing a thermally vaporizable composition as defined in claim 17, wherein the active ingredient is a dog and cat repellent.

27. A method of vaporizing a thermally vaporizable composition as defined in claim 17, wherein the active ingredient is a bird repellent.

28. A method of vaporizing a thermally vaporizable composition as defined in claim 17, wherein the active ingredient is a rodenticide.

29. A method of vaporizing a thermally vaporizable composition as defined in claim 17, wherein the active ingredient is a formicide.

30. A method of vaporizing a thermally vaporizable composition as defined in claim 17, wherein the solvent is at least one of aliphatic hydrocarbons having a boiling point in the range of about 150° to about 350° C.

31. A method of vaporizing a thermally vaporizable composition as defined in claim 17, wherein the solvent is at least one of glycerin, propylene glycol, methanol, acetone, benzene, xylene, chlorsen, isopropanol, solvent naphtha, methyl napthalene, aromatic naphtha and chloroform.

32. A method of vaporizing a thermally vaporizable composition as defined in claim 17, wherein the composition comprises about 3 to about 8% by weight of the active ingredient and about 0.3 to about 0.9% by weight of the compound.

* * * * *